(12) United States Patent
Sugiyama et al.

(10) Patent No.: US 11,085,913 B2
(45) Date of Patent: Aug. 10, 2021

(54) BIOLOGICAL SAMPLE ANALYZER

(71) Applicant: HITACHI HIGH-TECHNOLOGIES CORPORATION, Tokyo (JP)

(72) Inventors: Kiyotaka Sugiyama, Tokyo (JP); Tatsuo Nakagawa, Tokyo (JP); Iwao Suzuki, Tokyo (JP); Tsukasa Suenari, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 81 days.

(21) Appl. No.: 16/465,597

(22) PCT Filed: Oct. 10, 2017

(86) PCT No.: PCT/JP2017/036566
§ 371 (c)(1),
(2) Date: May 31, 2019

(87) PCT Pub. No.: WO2018/105224
PCT Pub. Date: Jun. 14, 2018

(65) Prior Publication Data
US 2019/0383793 A1    Dec. 19, 2019

(30) Foreign Application Priority Data
Dec. 9, 2016 (JP) .............................. JP2016-239094

(51) Int. Cl.
*G01N 33/49* (2006.01)
*G06T 7/90* (2017.01)
(Continued)

(52) U.S. Cl.
CPC ......... *G01N 33/491* (2013.01); *G01F 23/292* (2013.01); *G01N 21/27* (2013.01);
(Continued)

(58) Field of Classification Search
CPC .................. G01F 23/292; G01N 1/10; G01N 2035/00495; G01N 2035/00752;
(Continued)

(56) References Cited

U.S. PATENT DOCUMENTS

2003/0141456 A1    7/2003  Mc Neal et al.
2011/0045521 A1*   2/2011  Itoh ........................ G01N 35/04
                                                        435/29
(Continued)

FOREIGN PATENT DOCUMENTS

CN          105324671 A      2/2016
EP            3018482 A1     5/2016
(Continued)

OTHER PUBLICATIONS

Extended European Search Report received in corresponding European Application No. 17879379.0 dated Jun. 9, 2020.
(Continued)

*Primary Examiner* — Michael J Vanchy, Jr.
(74) *Attorney, Agent, or Firm* — Mattingly & Malur, PC

(57) ABSTRACT

A biological sample analyzer includes: a camera 201*a* imaging a blood collection tube 209 containing a biological sample; an image processing section 201*b* and a comparative analysis section 206 that analyze the image imaged by the camera in order to extract an existence region of the biological sample; a light source 203*a*1, a photo sensor 203*a*2 and a liquid-level position detection section 203*b* that detect the amount of transmitted light in the blood collection tube 209 in order to detect a liquid-level position of the biological sample; and the comparative analysis section 206 that, based on the extracted existence region of the biological sample and the detected liquid-level position of the biological sample, identifies a determination target portion for a category of the biological sample, and acquires color
(Continued)

information on the identified portion, in order to determine a category of the biological sample contained in the blood collection tube 209.

11 Claims, 9 Drawing Sheets

(51) Int. Cl.
    *G06T 7/00*        (2017.01)
    *G01N 35/00*      (2006.01)
    *G01F 23/292*    (2006.01)
    *G01N 21/27*      (2006.01)

(52) U.S. Cl.
    CPC ....... *G01N 35/0099* (2013.01); *G06T 7/0012* (2013.01); *G06T 7/90* (2017.01)

(58) Field of Classification Search
    CPC ... G01N 2035/0493; G01N 2035/1025; G01N 21/27; G01N 33/491; G01N 33/52; G01N 35/00732; G01N 35/0099; G01N 35/02; G01N 35/1009; G01N 35/00; G06T 7/0012; G06T 7/90
    See application file for complete search history.

(56) References Cited

U.S. PATENT DOCUMENTS

2016/0018427 A1\* 1/2016 Streibl .................... G01F 23/00
                                                                                                              702/19
2016/0109350 A1     4/2016 Esaki et al.

FOREIGN PATENT DOCUMENTS

| | | | |
|---|---|---|---|
| JP | 2004-037320 A | 2/2004 | |
| JP | 2004-37321 A | 2/2004 | |
| JP | 2011-247635 A | 12/2011 | |
| JP | 2012-159318 A | 8/2012 | |
| JP | 2012-159481 A | 8/2012 | |
| JP | 2015-014506 A | 1/2015 | |
| JP | 2016-008927 A | 1/2016 | |
| WO | 2015/002218 A1 | 1/2015 | |
| WO | WO-2015002218 A1 \* | 1/2015 | ........... G01N 15/042 |
| WO | 2015/056649 A1 | 4/2015 | |
| WO | WO-2015056649 A1 \* | 4/2015 | ............. G01N 15/05 |
| WO | 2015/159620 A1 | 10/2015 | |

OTHER PUBLICATIONS

International Search Report of PCT/JP2017/036566 dated Jan. 16, 2018.

\* cited by examiner

BIOLOGICAL SAMPLE ANALYZER

TECHNICAL FIELD

The present invention relates to a biological sample analyzer.

BACKGROUND ART

Along with the advance of automatic biochemical analyzers and automatic immuoanalyzers, there is progress in development of automated techniques to transfer and pre-process biological samples (specimens). An increase in the number of test items and the number of biological samples from year to year creates a market need for a system capable of being applied to diverse pre-processing of biological samples.

In typical biological sample tests, a dedicated container is prepared so that a patient's biological sample is collected into the container, followed by being pre-processed. A first example of pre-processing is the classification of states of biological samples into categories. For example, where a biological sample is blood, collected blood is loaded into blood collection tubes. Then, the blood collection tubes each undergo centrifugation in order to separate blood clots and serum from the blood, resulting in extraction of serum which is a component used in analysis. It is noted that these blood collection tubes are placed upright, for example, in a rack or the like, which are then subjected to analysis.

The rack in which the blood collection tubes are placed upright might contain both the blood collection tubes before undergoing the centrifugation (i.e., before separation of blood clots and serum), and the blood collection tubes having undergone centrifugation (i.e., after separation of blood clots and serum). Further, a separating agent might be previously held in a blood collection tube in order to obtain serum with less impurities. In such a case, blood collection tubes with a separating agent and blood collection tubes without a separating agent might be mixedly placed. Accordingly, the blood collection tubes containing various categories of biological samples are placed upright in the rack.

And, if hemolysis or turbidity occur in the separated serum, an accurate analysis result is sometimes not obtained in blood analysis which is based on the principle of measuring an absorbance. To avoid this, sorting operation is performed on serums contained in the blood collection tubes placed upright in the rack. As a result, such a blood collection tube is identified before being transferred to the automatic analyzer to carry out a measure, such as exclusion from the subsequent analysis, physical removal from the analysis line, or the like.

Under present circumstances those processing steps are carried out manually by a laboratory technician or the like. Specifically, the fact is that manpower is used to grasp, for example, states of the inside of a blood collection tube (existence/absence of centrifugation, existence/absence of separating agent, and the like), states of the separated serum, and the like. More specifically, a laboratory technician or the like actually check the inside of the blood collection tube to grasp the state of the inside of the blood collection tube and the state of the serum. As described above, however, as the number of test items and the number of specimens increase, the burdens on laboratory technicians and the like are increased. To address this, there is a need for a technology to grasp the states of the inside of a biological sample storing container, such as a blood collection tube and the like, for the purpose of automatically finding a category of the biological sample.

In connection with such technology, a technique described in Patent Literature 1 is known. Patent Literature 1 describes that a detector performs detection on a container in which a sample including a first component and a second component is stored. It is also described that the detector includes an imaging unit to image the container, a background unit providing a background to the imaging unit, and a sensing unit to sense a color of the first component of the sample. It is then described that the container is placed between the imaging unit and the background unit. And, it is described that the sensing unit is configured to recognize a first region of the first component against a background of a label affixed to the container, and a second region of the first component against a background of the background unit, and then to detect color information relating to the first component from at least one of the first and second regions.

CITATION LIST

Patent Literature

Patent Literature 1: Japanese Patent Application Publication No. 2015-14506 (in particular, see "abstract" in Abstract)

SUMMARY OF INVENTION

Technical Problem

Where a biological sample is blood, in most cases a blood collection tube bears a label with a barcode printed thereon to identify a patient. Then, a label often gives, for example, information printed thereon for use in analysis, in addition to the information to identify a patient, and sometimes multiple labels are affixed. That is, there is a trend toward an increase in region for affixation of a label. Due to this, for example, a label may be affixed to almost the entire periphery of the blood collection tube.

In this case, the technique described in Patent Literature 1 uses a camera to acquire a two-dimensional image for the unlabeled part (a gap between the ends of the label in the circumferential direction) (e.g., see paragraph 0020 and the like in Patent Literature 1). Then, image analysis is performed on the acquired two-dimensional image in order to obtain color information on serum and information relating the amount of serum (e.g., see paragraph 0027 and the like in Patent Literature 1).

However, when an image is taken by a camera, a category of the serum may possibly not be correctly determined depending on a direction or an amount of light projected toward the inside of a blood collection tube. In particular, if broadening the labeled region narrows the unlabeled part (i.e., a gap between the ends of a label in the circumferential direction), combined with susceptibility to color of the label, a category of the serum may possibly not be correctly determined. Accordingly, the technique described in Patent Literature 1 still has an issue on a degree of accuracy with which a type of a biological sample, such as serum or the like, is found when, in particular, the broadening of the labeled region makes it difficult to make a manual visual check of the inside of a container, such as a blood collection tube.

The present invention has been achieved in view of the problems and a problem to be solved by the present invention is to provide a biological sample analyzer which is capable of accurately finding a category of a biological sample even if broadening of a labeled region of a biological sample tube or a reduction in size of a biological sample tube makes it difficult to make a manual visual check of the inside of the biological sample tube.

Solution to Problem

As a result of diligently studying to solve the above problems, the inventors have gained the following knowledge to reach the present invention. Specifically, a subject-matter of the present invention relates to a biological sample analyzer that includes: an imaging device that images a biological sample tube containing a biological sample; an image analysis device that analyzes the image imaged by the imaging device in order to extract an existence region of the biological sample within the biological sample tube; a liquid-level position detector that emits light toward the biological sample tube from outside the biological sample tube to detect the amount of transmitted light from the biological sample tube, thereby detecting a liquid-level position of the biological sample within the biological sample tube; and a comparative analysis device that, based on the existence region of the biological sample extracted by the image analysis device and also on the liquid-level position of the biological sample detected by the liquid-level position detector, identifies a determination target portion for a category of the biological sample, the comparative analysis device then acquiring color information on the identified portion in order to determine a category of the biological sample contained in the biological sample tube.

Advantageous Effects of Invention

According to the present invention, it is possible to provide a biological sample analyzer which is capable of accurately finding a category of a biological sample even if broadening of a labeled region on a biological sample tube or a reduction in size of a biological sample tube makes it difficult to make a manual visual check of the inside of the biological sample tube.

DESCRIPTION OF EMBODIMENTS

Although a mode for carrying out the present invention (the embodiment) will be described below with reference to the accompanying drawings as appropriate, the present invention is not limited to any of the following examples. It is noted that a biological sample analyzer according to the embodiment will be described using a blood collection tube as an example of the biological sample tube, unless otherwise specified, in the following description.

First, in a biological sample analyzer 100 (described later) in accordance with a first embodiment, a category of a biological sample contained in a blood collection tube is acquired with accuracy by performing a comparison between an existence position of the biological sample (serum or the like) and a liquid-level position of the biological sample (serum or the like), the existence position being detected by analyzing an image taken by a camera 201*a* (described later), the liquid-level position being detected by use of infrared light. That is, the biological sample analyzer 100 performs both software-based analysis and hardware-based analysis on a blood collection tube 209 (described later). Then, this makes it possible to find a category of a biological sample accurately with a slight gap (between the ends of label in the circumferential direction of a blood collection tube) even if a large-sized label 306 (described later) is affixed to the surface of the blood collection tube 209 such that a laboratory technician or the like can hardly check the inside of the blood collection tube 209.

Figure 1:
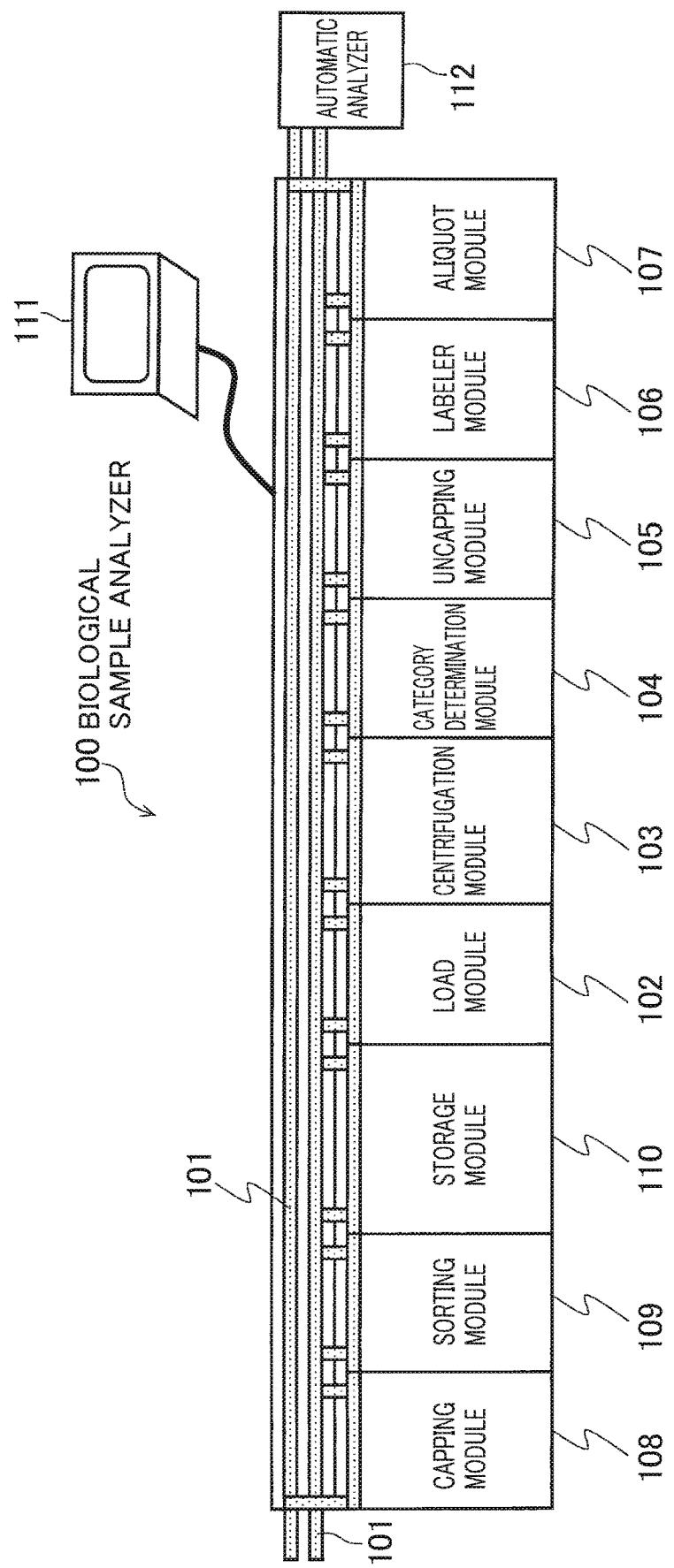
FIG. 1 is a general diagram of a biological sample analyzer in accordance with a first embodiment.

FIG. 1 is a general diagram of the biological sample analyzer 100 in accordance with the first embodiment. The biological sample analyzer 100 is configured to include a transfer line 101, a load module 102, a centrifugation module 103, a category determination module 104, a uncapping module 105, and a labeler module 106 that prints and affixes a barcode to an empty blood collection tube (not shown) which differs from the blood collection tube 209 containing a biological sample (see FIG. 2, not shown in FIG. 1). The biological sample analyzer 100 is also configured to include an aliquot module 107, a capping module 108, a sorting module 109 and a storage module 110. Also, the biological sample analyzer 100 is connected to a control personal computer 111 and an automatic analyzer 112 via an input/output I/F 207 (see FIG. 2, not shown in FIG. 1) which is included in the biological sample analyzer 100, the control personal computer 111 controlling the biological sample analyzer 100, the automatic analyzer 112 analyzing a component of serum within the blood collection tube 209.

Next, a series of process steps to pre-process and analyze a biological sample is described. First, blood (biological sample) collected from a patient (test subject) is placed in a blood collection tube 209, and then loaded into the load module 102. A label 306 of a certain large size (see FIG. 3(b)) is affixed to the blood collection tube 209 loaded at this stage, causing the inside of the blood collection tube 209 to be difficult to be visually checked. In general, collecting blood and loading the blood collection tube 209 into the load module 102 are performed manually by a laboratory technician or the like. The blood collection tube 209 is then placed on the transfer line 101 to be moved among the centrifugation module 103, category determination module 104, uncapping module 105, labeler module 106, aliquot module 107, capping module 108, sorting module 109 and the storage module 110.

In the centrifugation module 103, centrifugation is performed on the loaded blood (biological sample). After the centrifugation, there is separation between a blood-clot layer of relatively higher specific gravity and a serum layer of relatively lower specific gravity which is used in component analysis. The layers (blood-clot and serum layers) contain water content and blood cells which absorb infrared light.

Subsequently, in the category determination module 104, detections of a biological sample category and the amount of biological sample is performed on the biological sample (blood). Specifically, the amount of serum to be analyzed by the aforementioned automatic analyzer 112 is detected. At this stage, if the biological sample is determined as hemolysis and/or is extremely small in amount, the blood collection tube 209 containing the biological sample in question is moved to the sorting module 109, and is classified as an error specimen. On the other hand, if the biological sample is not determined as hemolysis and the amount of serum is adequate, the blood collection tube 209 on which component analysis is to be performed is moved to the uncapping module 105 by the transfer line 101.

In the uncapping module 105, a cap 300 (see FIG. 3, not shown in FIG. 2) of the blood collection tube 209 is removed. In the labeler module 106, a label (not shown) is affixed to an empty container (not shown), the label with a printed barcode or the like which represents a determination result by the category determination module 104, which will be detailed later. In the aliquot module 107, the blood collection tube 209 after the centrifugation (primary specimen) is aliquoted into not-shown, unlabeled blood collection tubes (secondary specimens, not shown) for analysis in the automatic analyzer 112 and/or the like. In the capping module 108, the blood collection tubes of the respective primary and secondary specimens are capped. In the sorting module 109, the primary specimen and the secondary specimens are sorted, so that the primary specimen is moved to the storage module 110 and the secondary specimens are moved to the automatic analyzer 112 to perform analysis for various components.

Figure 2:
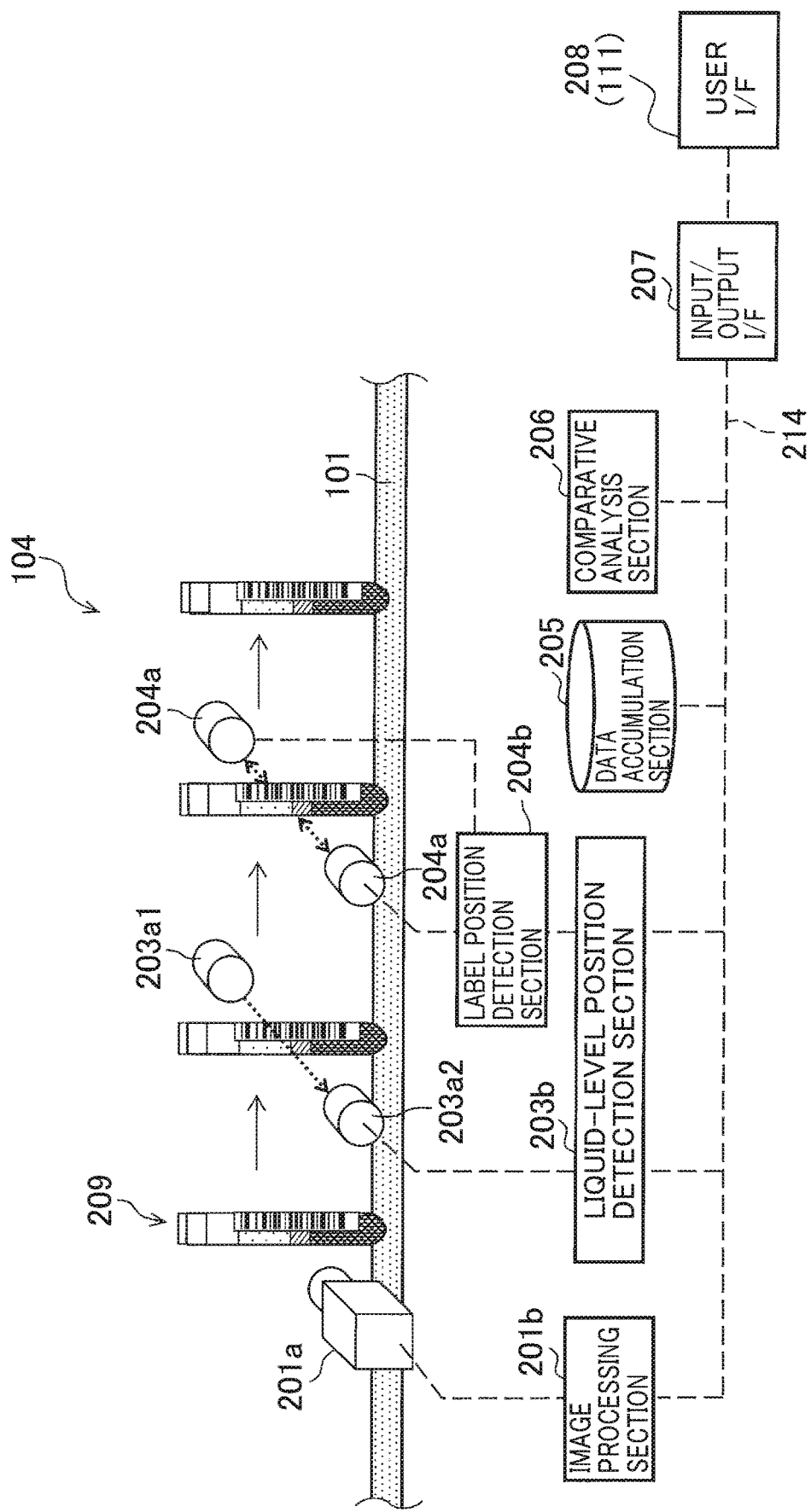
FIG. 2 is a diagram illustrating a detector installed in the biological sample analyzer in accordance with the first embodiment.

FIG. 2 is a diagram illustrating the category determination module 104 installed in the biological sample analyzer 100 in accordance with the first embodiment. The category determination module 104 comprises: an image processing section 201b that has a camera 201a; and a liquid-level position detection section 203b that has a light source 203a1 and a photoreceptor 203a2, the light source 203a1 irradiating the blood collection tube 209 with infrared light, the photo sensor 203a2 receiving the infrared light passing through the blood collection tube 209. The category determination module 104 also comprises a label position detection section 204b that has light emitter/receptors 204a, which emits visible light to the blood collection tube 209 with visible light and also receives the light reflected from the blood collection tube 209. The two light emitter/sensors 204a are coaxially placed on the opposite sides of the blood collection tube 209 from each other, thereby achieving detection of a label position with high accuracy.

The category determination module 104 further comprises: a data accumulation section 205 that accumulates data obtained by the image processing section 201b, the liquid-level position detection section 203b and the label position detection section 204b; a comparative analysis section 206 that performs comparative analysis on the obtained data; an input/output I/F (interface) 207; and a user I/F 208, all of which are connected to each other through an electric signal line 214 which is shown by the broken line in FIG. 2.

Various items of information obtained by the category determination module 104 (such as positional information on boundary surfaces 502, 503 (see FIG. 5) extracted through image analysis, positional information on serum (see FIG. 6) obtained by the liquid-level position detection section 203b, color information on serum (see FIG. 7), etc.) are transmitted to a laboratory technician or the like. Specifically, such information is transmitted to a laboratory technician or the like via the input/output I/F 207 (e.g., a USB terminal, a LAN port and/or the like) and the user I/F 208 which are installed in the category determination module 104.

The terms "laboratory technician or the like" as used herein do not necessarily mean a laboratory technician or the like who is present close to the biological sample analyzer 100, but rather mean a laboratory technician or the like who is able to operate the user I/F 208 vie the input/output I/F 207. Because of this, the biological sample analyzer 100 may be operated by the laboratory technician or the like at a remote location by air or through the internet.

Examples of the user I/F 208 include various types of devices installed in the aforementioned control personal computer 111 and the operations of the devices, such as, specifically, a mouse, a keyboard, a touch panel, a display, turning-on of a lamp, a warning beep from a speaker, and the like. The user I/F 208 is used to input a parameter, a threshold value and the like which are used, for example, in display of a detected biological sample category and the detected amount of biological sample, in detection of a biological sample category and the amount of biological sample, and the like. It is noted that the user I/F 208 illustrated in FIG. 2 corresponds to the aforementioned control personal computer 111 described with reference to FIG. 1.

The image processing section 201*b*, the liquid-level position detection section 203*b*, the label position detection section 204*b*, the data accumulation section 205 and the comparative analysis section 206 all of which installed in the biological sample analyzer 100 are also configured at least partially independently of each other or in combination to include a CPU (Central Processing Unit), RAM (Random Access Memory), ROM (Read Only Memory), HDD (Hard Disk Drive), and the like, each of which is not shown. And, these sections are implemented by the CPU executing a predetermined control program stored in the above-described ROM.

In the category determination module 104, comparative analysis is performed on a boundary surface position of the biological sample acquired by the image processing section 201*b*, and a liquid-level position of the biological sample obtained by the liquid-level position detection section 203*b*, in order to determine the category (normal, hemolysis, jaundice or chyle) of the serum within the blood collection tube 209. The determination is made by the comparative analysis section 206, which will be described later in detail. Also, because the cross-sectional area of the blood collection tube 209 is known before analysis, the liquid volume of serum can be measured by finding the liquid-level position of the serum.

Then, the series of detection operations is performed by causing the blood collection tube 209 placed on a holder (not shown) to move on the transfer line 101. It should be understood that the camera 201*a*, the light source 203*a*1, the photosensor 203*a*2 and the light emitter/receptors 204*a* are illustrated in this order in FIG. 2, but the order of detections to be performed is not limited to the above-described order.

Figure 3:
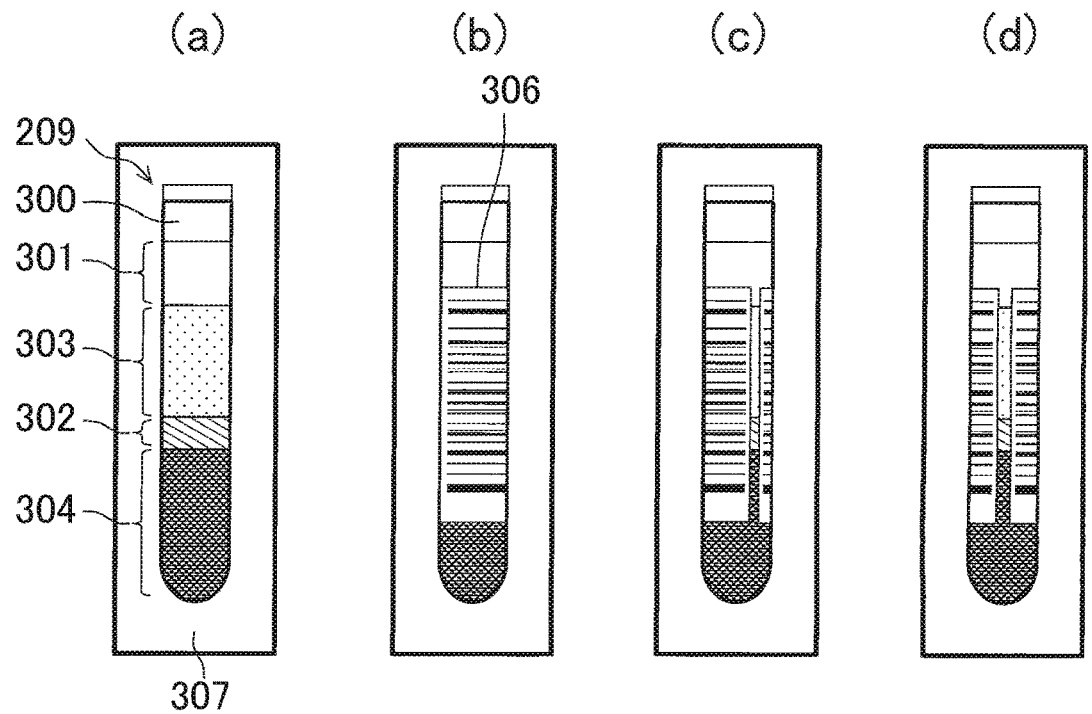
FIG. 3 illustrate images imaged by a camera installed in the detector illustrated in FIG. 2, in which (a) is a diagram depicting an appearance of a biological sample tube determined as no label, (b) is a diagram depicting an appearance of a biological sample tube with a label on the camera side, (c) is a diagram depicting an appearance of a biological sample tube mostly covered with a label on the image, and (d) is a diagram depicting an appearance of a biological sample tube with a clearly discernible gap created between both ends of a label.

FIG. 3 illustrate images taken by the camera 201*a* installed in the category determination module 104 illustrated in FIG. 2, in which (a) is a diagram depicting the blood collection tube 209 determined as no label 306, (b) is a diagram depicting an appearance of the blood collection tube 209 bearing the label 306 on the camera 201*a* side, (c) is a diagram depicting an appearance of the blood collection tube 209 mostly covered with the label 306 on the image, and (d) is a diagram depicting an appearance of the blood collection tube 209 with a clearly discernible gap created between both ends of the label 306.

Figure 8:
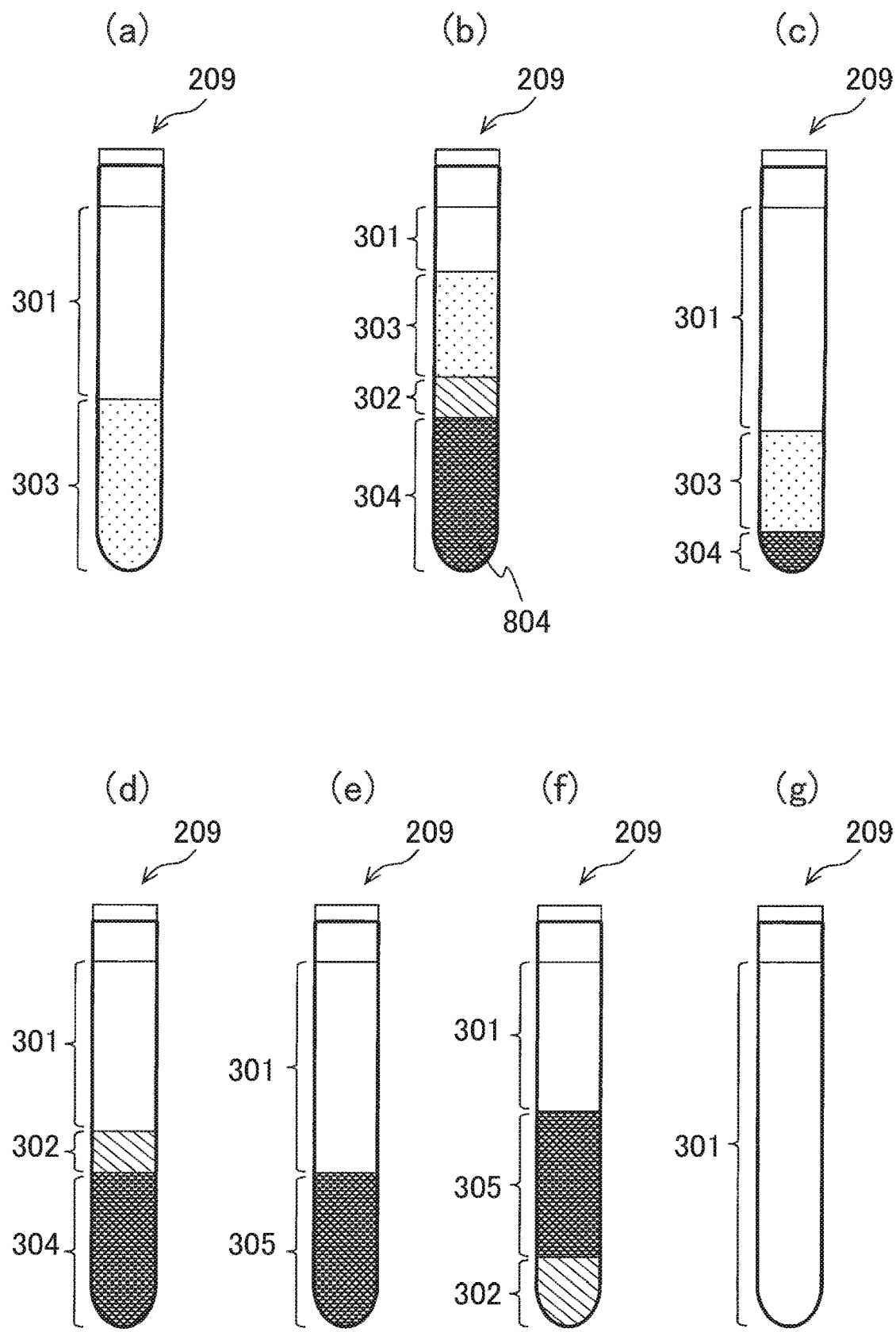
FIG. 8 represent blood collection tubes to be subjected to analysis in a biological sample analyzer in accordance with a second embodiment, in which: (a) represents the blood collection tube containing only serum; (b) represents the blood collection tube containing serum, a separating agent and blood clots; (c) represents the blood collection tube containing serum and blood clots; (d) represents the blood collection tube containing a separating agent and blood clots; (e) represents the blood collection tube containing only blood clots; (f) represents the blood collection tube containing blood and a separating agent; and (g) represents the empty blood collection tube.

Blood 305 (see FIG. 8(*f*), not shown in FIG. 3) is collected by use of a blood collection tube 209 into which a separating agent 302 is sealed, and then the specimen having been subjected to centrifugation exhibits an arrangement illustrated in FIG. 3(*a*). It is noted that FIG. 3(*a*) illustrates the blood collection tube 209 bearing no label 306 as described above for the purpose of showing the state in the blood collection tube 209 after the centrifugation. And, as illustrated in FIG. 3(*a*), the blood sealed into the blood collection tube 209 is separated into an upper region of serum 303 and a lower region of blood clots 304 by the separating agent 302. Air 301 also exists in an upper portion of the blood collection tube 209. And, the cap 300 is placed on the blood collection tube 209 so that the blood collection tube 209 is sealed to prevent leakage of the biological sample.

Also, in actuality, because the label 306 is affixed to the blood collection tube 209 as described above, depending on the positional relationship between the camera 201*a* (see FIG. 2) and the blood collection tube 209, a portion corresponding to the serum 303 might be covered with the label 306 as illustrated in FIG. 3(*b*). Therefore, to address such an event, the blood collection tube 209 is rotated in the circumferential direction by a biological sample tube rotating device which is not shown. Specifically, in the biological sample analyzer 100, from the viewpoint of detection at high speed, while the blood collection tube 209 is being rotated by the biological sample tube rotating device, the blood collection tube 209 is continuously imaged by the camera 201*a* secured to the biological sample analyzer 100. This changes the positional relationship between the camera 201*a* and the blood collection tube 209, and therefore, imaged is a site where the serum 303 is at least partially viewed through a gap which is created between the both ends of the label 306 in the circumferential direction (FIG. 3(*c*) and FIG. 3(*d*)). The word "continuously" as used herein may refer to "acquisition of multiple images" or to "moving images"

It is preferable that a white or black background 307 is placed behind the blood collection tube 209 for the purpose of achieving smooth image processing which will be described later. Then, the image taken at this stage is input to the image processing section 201*b*.

Figure 4:
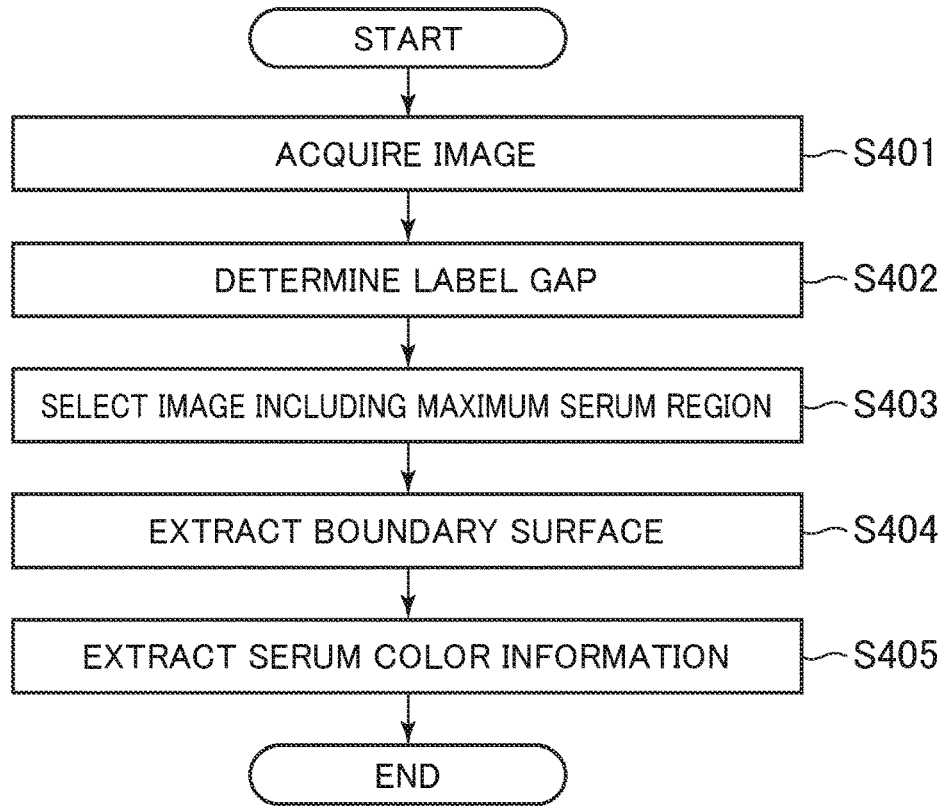
FIG. 4 is a flow diagram illustrating image analysis performed in the biological sample analyzer in accordance with the first embodiment.

FIG. 4 is a diagram illustrating a flow of the image analysis performed in the biological sample analyzer 100 in accordance with the first embodiment. The flow will now be described with reference to FIG. 2 and FIG. 3 as appropriate. First, the blood collection tube 209 is continuously imaged by the camera 201*a* to acquire two-dimensional images (step S401). The images taken at this stage may be, for example, the images illustrated in FIG. 3(*b*) to FIG. 3(*d*). The imaged image data is transmitted to the image processing section 201*b* for the subsequent processing.

Subsequently, the image processing section 201*b* makes a determination about a gap of the label 306 on the basis of the received images (step S402). Specifically, the image processing section 201*b* determines whether or not a gap is created between the both ends of the label 306 in the circumferential direction. For example, the above-described images illustrated in FIG. 3(*c*) and FIG. 3(*d*) correspond to the case where a gap is created. Here, the image processing section 201*b* performs image processing for removing a region of the background 307. Also, although a barcode label, letters, numerics and/or the like are printed on the surface of the label 306, the color of the label 306 is often white. Because of this, the gap of the label 306 can be easily determined by edge extraction processing using Pixel Value Differentiation and/or the like.

It is noted that, if the gap of the label 306 is not found in step S402, the flow in FIG. 4 cannot continue to the subsequent processing, but this is omitted in the flow illustrated in FIG. 4 for the sake of simplification of description. As a result, the procedure is terminated before extraction of color information which will be described later. At this stage, in some cases, the blood collection tube 209 in question is removed from the biological sample analyzer 100 without being subjected to subsequent analysis in the biological sample analyzer 100, and then the laboratory technician or the like make a visual inspection of the blood collection tube 209 in question.

In step S402 as described above, after the existence of the gap of the label 306 is confirmed, the image processing section 201b selects a single image from among a plurality of imaged images, the single image including the largest area of the serum region, that is, the largest area of the uppermost located region of the regions of the biological sample (the existence region of the biological sample) (step S403). For example, where a plurality of images as illustrated in FIG. 3(b) to FIG. 3(d) is acquired, the image corresponding to FIG. 3(d) is selected to perform the subsequent processing. Differentiation of each layer and the area of each layer may be calculated by, for example, the above-described edge extraction processing or the like. The step S403 is performed together with the subsequent step S404. Specifically, during the differentiation of each boundary surface, the area of each layer is calculated.

It is noted that, in this stage, where a biological sample, for instance, jaundice or the like, is apt to adhere to the inner wall of the blood collection tube 209, although the actual amount of biological sample is not so large, it may possibly be determined that the area thereof on the image measured by the camera 201a is maximum. In this case, the blood collection tube 209 containing such a biological sample will be detected even when a detection is performed on a liquid-level position by the liquid-level position detection section 203b which will be described later (detailed later with reference to FIG. 7). And, in such a case, a correction will be made by a liquid-level position physically detected. Therefore, it does not matter if such a detection error is included in step S403 described here and step S404 described later.

Subsequently, the image processing section 201b extracts a boundary surface from the image including the maximum area of the serum region (e.g., FIG. 3(d) described above) (step S404). Specifically, a boundary surface of each layer is extracted in the image including the maximum area of the serum region, which is described above in step S403.

Here, where the separating agent is sealed in the blood collection tube 209 and also the centrifugation is performed on the same, in the blood collection tube 209 the boundary surface of the biological sample is any one of the air-serum boundary surface, the serum-separating agent boundary surface and the separating agent-blood clot boundary surface. Each boundary surface exists in a direction perpendicular to the length direction of the blood collection tube 209 (i.e., the boundary surface is horizontal to the blood collection tube 209 in an upright position). Because of this, each boundary surface is able to be detected through the edge extraction processing using Pixel Value Differentiation in the longitudinal direction of the blood collection tube 209, and the like. Also, the region of the serum 303 is located above the region of the separating agent 302 and the region of the blood clots 304. From this fact, it is possible in this step S404 to extract the boundary surface between air and the serum, that is, a region in which the serum exists.

It is noted that, if the boundary surface is not detected in this stage, this means that there is no boundary surface. In other words, the blood collection tube is empty (see FIG. 8(g) described later). Accordingly, in this case, the procedure is terminated without performing the subsequent processing. In this case, the blood collection tube 209 in question is removed from the biological sample analyzer 100 without being subjected to subsequent analysis in the biological analyzer 100.

Lastly, the image processing section 201b extracts color information on serum for at least one pixel in the serum region obtained in an image resulting from the image processing (step S405). Then, at least one piece of the extracted color information may be used to exclude the influence of letter information and/or numeric information printed on the surface of the blood collection tube 209 (e.g., manufacturing lot number and model number of the blood collection tube 209). At this stage, in terms of higher accuracy, two or more pieces of the color information are preferably extracted to calculate and use a mean value of the pixel values, a median value of the pixel values, a pixel variance value or the like of the pixel. Based on the color information extracted here, a category of serum (normal, hemolysis, jaundice or chyle) is able to be determined. Incidentally, a specific method of extracting color information will be described later with reference to FIG. 7.

Figure 5:
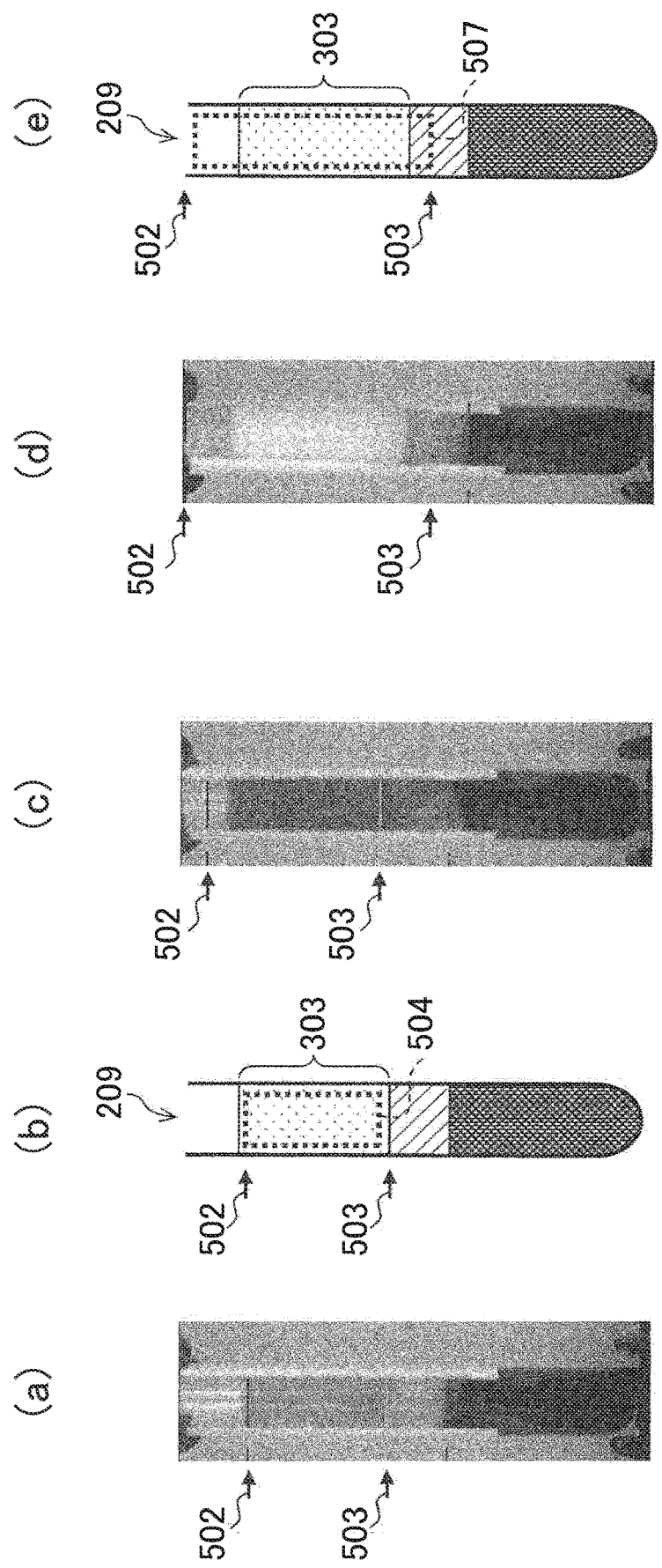
FIG. 5 illustrate diagrams for explaining boundary surface positions obtained through the flow illustrated in FIG. 4, in which (a) is a drawing substitute photograph concerning normal serum, (b) is a diagram illustrating boundary surfaces obtained through the image analysis of (a) and a serum region defined by the boundary surfaces, (c) is a drawing substitute photograph concerning serum determined as jaundice, (d) is a drawing substitute photograph concerning serum determined as chyle, and (e) is a diagram illustrating boundary surfaces obtained through the image analysis of (d) and a serum region defined by the boundary surfaces.

FIG. 5 illustrate diagrams for explaining the positions of the boundary surfaces, 502 and 503 obtained through the flow illustrated in FIG. 4, in which (a) is a drawing substitute photograph concerning normal serum, (b) is a diagram illustrating the boundary surfaces 502, 503 obtained through the image analysis of (a) and a region 504 defined by the boundary surfaces 502, 503, (c) is a drawing substitute photograph concerning serum determined as jaundice, (d) is a drawing substitute photograph concerning serum determined as chyle, (e) is a diagram illustrating the boundary surfaces, 502 and 503 obtained through the image analysis of (d) and a serum region 507 defined by the boundary surfaces 502 and 503. In FIG. 5, also, reference signs representing the blood clots and the separating agent (respectively indicated by 304, 302) are omitted for the sake of simplified illustration.

FIG. 5(a) illustrates the actual inside of a blood collection tube 209 after blood has been placed in the blood collection tube 209 containing the separating agent 302 and then subjected to centrifugation. On the other hand, in FIG. 5(a), the arrows indicate the positions of the boundary surfaces 502 and 503 obtained through the above-described flow illustrated in FIG. 4 (i.e., the positions of the boundary surfaces 502 and 503 obtained through the image analysis performed by the above-described comparative analysis section 206 illustrated in FIG. 2). As illustrated in FIG. 5(a), it is seen that the actual positions of the upper and lower boundary surfaces of the serum (the positions of the upper and lower interfaces of the serum in the drawing substitute photograph shown in FIG. 5(a)) nearly match the boundary surfaces 502 and 503 obtained through the image analysis. The term "match" as used here refers to a match of positions in the length direction (height direction) of the blood collection tube 209.

As illustrated in FIG. 5(b), the region 504 defined by the boundary surfaces, 502 and 503 obtained through the image analysis is included in the region of the actual serum 303. Therefore, by extracting the color information from within the region 504, the color information on the serum is extracted with reliability. Also, because, as described above, the actual boundary surfaces (the positions on the drawing substitute photograph shown in FIG. 5(a)) nearly match the boundary surfaces, 502 and 503 obtained through the image analysis, the amount of serum is also able to be found with accuracy by calculating the area of the region 504.

Subsequently, the serum determined as jaundice (FIG. 5(c)) and the serum determined as chyle (FIG. 5(d)), resulting from component analysis separately performed in advance, are used to perform the image processing along the above-described flow in FIG. 4. And, the boundary surfaces, 502 and 503 obtained through the image analysis are respectively applied to FIG. 5(c) and FIG. 5(d). And, FIG. 5(e) shows a schematic representation of the region 507 delimited by the boundary surfaces, 502 and 503.

As illustrated in FIG. 5(e), a portion not included in the actual region of the serum 303 exists in the region 507 delimited by the serum boundary surfaces, 502 and 503 extracted by the image analysis. That is, the region 507 delimited by the boundary surfaces 502 and 503 of the serum 303 extracted by the image analysis falls outside the region of the actual serum 303. Thus, extracting color information from within the region 507 does not always result in extraction of color information from the region of the serum 303. For example, a color of a region other than the serum 303 (e.g., the background of the air 301 (reference sign omitted in FIG. 5, see FIG. 3(a)) might be erroneously extracted instead of the color of the serum.

Further, the jaundiced serum and the chylous serum are used herein by way of example only. However, unlike the above-described region 504, as regards any biological sample in another state, the region 507 delimited by the serum boundary surfaces, 502 and 503 extracted by the image analysis might also fall outside the region of the biological sample, as described above. For example, in the case of a turbid biological sample of a whitish color close to the color of the label 306 (see FIG. 3(b), not shown in FIG. 5), the ends of the label 306 might be incorrectly determined as a boundary surface. In another example, for reasons of a high affinity for the inner wall of the blood collection tube 209 and/or the like, such a phenomenon is apt to occur in a biological sample that is apt to adhere to or remain near the inner wall of the blood collection tube 209. Therefore, in these cases, an incorrect color of serum is likely to be extracted depending on image analysis.

As described above, however, in this case, when the liquid-level position detection section 203b, described later, detects the liquid-level position, the blood collection tube 209 containing such a biological sample will be detected. Then, in such a case, correction is made by use of a liquid-level position physically detected (which will be described later in detail). Accordingly, it does not matter if step S403 and step S404 described above include such a detection error. And, in the biological sample analyzer 100 in accordance with the first embodiment, in addition to the above image analysis, hardware is used to perform physical liquid-level detection without reliance on image analysis.

Figure 6:
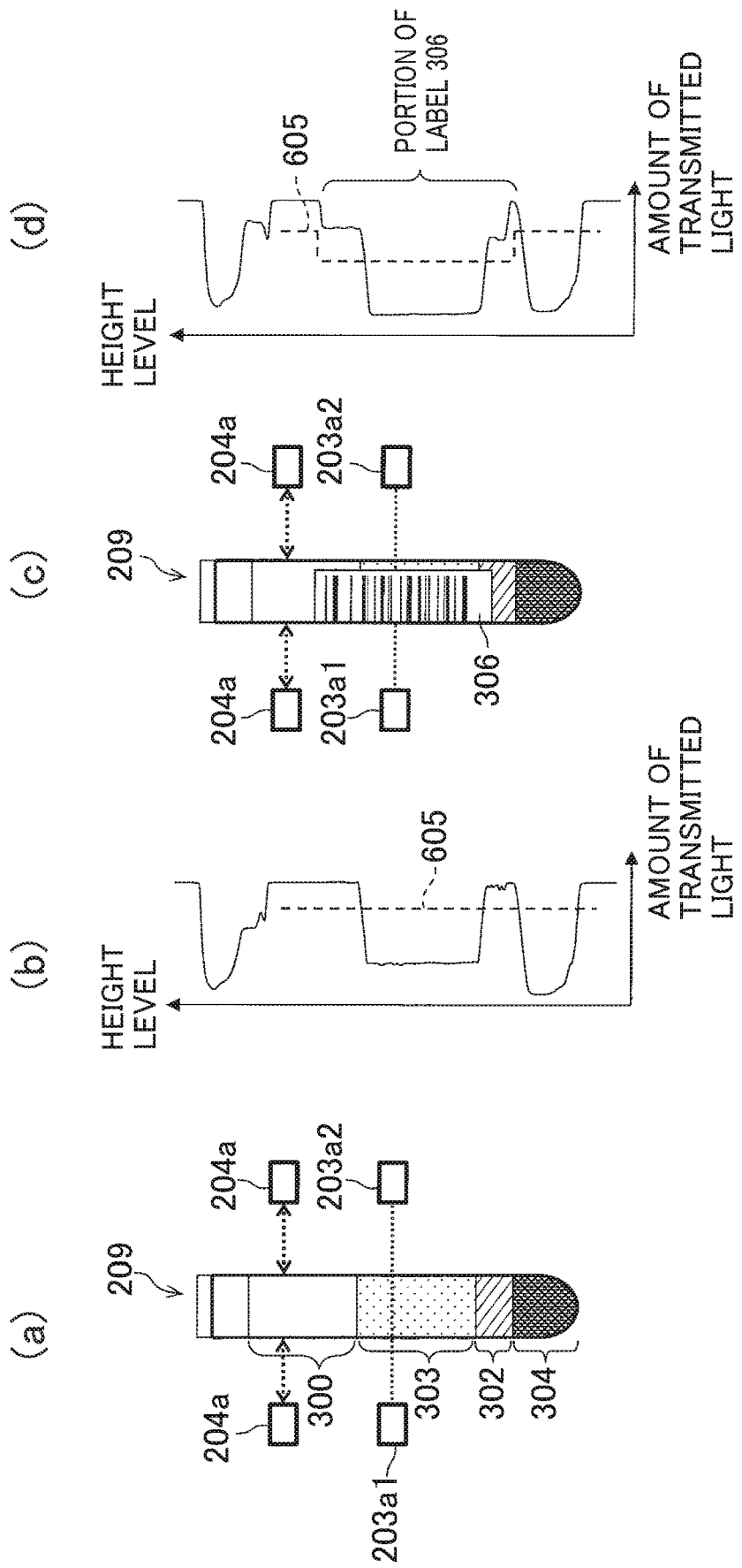
FIG. 6 illustrate diagrams explaining how to determine a liquid-level position by use of laser light in the biological sample analyzer in accordance with the first embodiment, in which (a) is a diagram illustrating the situation of performing the determination on an unlabeled blood collection tube, (b) is a graph showing the relationship between the amount of transmitted light and the position in the length direction of the blood collection tube in (a), (c) is a diagram illustrating the situation of performing the determination on a labeled blood collection tube, and (d) is a graph showing the relationship between the amount of transmitted light and the position in the length direction of the blood collection tube in (c).

FIG. 6 illustrate diagrams explaining how to determine a liquid-level position by use of laser light in the biological sample analyzer 100 in accordance with the first embodiment, in which (a) is a diagram illustrating the situation of performing the determination on the blood collection tube 209 without label 306, (b) is a graph showing the relationship between the amount of transmitted light and the position in the length direction of the blood collection tube 209 (i.e., the height level) of (a), (c) is a diagram illustrating the situation of performing the determination on the labeled blood collection tube 209 bearing the label 306, and (d) is a graph showing the relationship between the amount of transmitted light and the position in the length direction of the blood collection tube 209 (i.e., the height level) of (c). It is noted that the above-described FIG. 2 shows the light source 203a1, the photo sensor 230a2 and the light emitter/receptors 204a, 204a detecting the label position, as independent components, but FIG. 6 show them as a combination on the same drawing for the sake of convenience.

In FIG. 6(a), the light source 203a1 and the photo sensor 203a2 are placed on the opposite side of each other from the blood collection tube 209 containing a biological sample to detect only the infrared light passing through the biological sample. The light source 203a1 used herein is a laser. Using such light with high directivity enables more accurate detection of a liquid-level position. In particular, by using the light source 203a1 with a large amount of light emission such as a laser, even if the label 306 covers the entire periphery of the blood collection tube 209, the passage through the label 306 facilitates the detection of the liquid-level position in the blood collection tube 209. On the other hand, a halogen lamp, LED and the like as well as a laser can be used as the light source 203a1.

The wavelength of the light emitted from the light source 203a1 is that of infrared light as described above, which is specifically, for example, 0.7 μm or greater, preferably, 1 μm or greater, and the upper limit is 2.5 μm or less, preferably, 2 μm or less. Using the infrared light having such a wavelength range enables taking advantage of properties of: the light being mostly absorbed by a blood cell component contained in the blood clots 304, water content contained in the serum. 303, and the like; and on the other hand, the light mostly passing through a resin gel component used often in the separating agent 302.

And, as a result, a more abrupt change in signal is able to be detected in the boundary surface between the blood clots 304 and the separating agent and the interface surface between the separating agent 302 and the serum 303. That is, the use of infrared light enables more reliable detection of a liquid-level position. Further, the amount of transmitted light varies depending on the components and the volume of the biological sample, and therefore, even if the biological sample is apt to adhere to or remain near the inner wall of the blood collection tube 209, a highly accurate detection of a liquid-level position can be achieved by detecting the liquid-level position on the basis of the amount of transmitted infrared light. Then, by the accurate detection of the liquid-level position, the color information on the serum 303 is able to be correctly acquired and the category of the serum 303 is able to be accurately determined as described above with reference to FIG. 5.

Further, where the separating agent 302 is a gel resin, the color of the separating agent 302 is often close to a white color, and resembles the color of the label 306 and the color of the chylous serum 303. Because of this, depending on the state of the serum 303 or a way of the label 306 affixed, only the image analysis makes the separating agent 302 and the serum 303 indistinct from each other, and therefore the category of the serum 303 might be misidentified. However, by additionally employing the method illustrated in FIG. 6, such an error can be prevented to detect the liquid-level position with high accuracy.

The biological sample analyzer 100 also includes a biological sample tube moving device (not shown) to move the blood collection tube 209 in the up-down directions relative to the light source 203a1 and the photo sensor 203a2 which are fixed to the biological sample analyzer 100. Therefore, while the blood collection tube 209 is moved at least one of the up and down directions by the biological sample tube moving device, the light amount of infrared light passing through (the amount of transmitted light) is measured. Hence, a profile of the amount of transmitted light in the length direction (FIG. 6(b), described later) is obtained. It is noted that the profile obtained here is accumulated in the data accumulation section 205 through the liquid-level position detection section 203b.

In addition, in the biological sample analyzer 100, an affixation position of the label 306 is detected when the profile is created. Specifically, when the above-described biological sample tube moving device moves the blood collection tube 209 in at least one of the up and down directions relative to the light emitter/receptors 204a, 204a fixed to the biological sample analyzer 100, a change in the amount of light reflected in the blood collection tube 209 is measured. As compared with the unlabeled portion, the amount of reflection of light (visible light) is changed in the portion to which the label 306 is affixed. Because of this, by measuring the amount of reflection, the existence or absence of the label 306 in the light-irradiated portion can be determined. And, the determination is made for the entire area in the length direction of the blood collection tube 209 in order to detect the affixation position of the label 306. It is noted that the affixation position of the label 306 obtained at this stage is accumulated in the data accumulation section 205 through the label position detection section 204b and the liquid-level position detection section 203b.

FIG. 6(b) is a profile of the amount of transmitted light acquired by the above-described photo sensor 203a2. Most of the infrared light passes through the region of the air 301 (see FIG. 3(a)) above the liquid level of the blood collection tube 209, and also passes through the region of the separating agent 302, and therefore, in the two regions, the amount of transmitted light increases. On the other hand, in the region of the blood clots 304 containing the blood cell component and the region of the serum 303 containing water, the infrared light is absorbed and therefore the amount of transmitted light decreases.

In contemplation of this, a predetermined threshold value 605 is provided so that a portion where the amount of transmitted light exceeds the threshold value and also which is located in an upper portion in the length direction of the blood collection tube 209 (i.e., a portion at a higher height level) can be determined can be determined as a region containing the air 301. Likewise, a portion where the threshold value 605 is not exceeded and also which is located in an upper portion in the length direction of the blood collection tube 209 can be determined as a region corresponding to the serum 303. Further, a portion where the threshold value is exceeded and which is located in a lower portion in the length direction of the blood collection tube 209 (i.e., a portion at a lower height level) can be determined as a region corresponding to the separating agent 302. And, a portion where the threshold value 605 is not exceeded and also which is located in a lower portion in the length direction of the blood collection tube 209 can be determined as a region corresponding to the blood clots 304. In short, the liquid-level position of the biological sample is determined by performing a comparison between the amount of transmitted infrared light and the threshold value 605. Then, if the liquid-level position of the biological sample, that is, the length of the biological sample in the length direction of the blood collection tube 209 (i.e., a position in the height direction) are determined, the amount of each biological sample (particularly, the serum 303) can be also found.

Also, the example where the label 306 is not affixed has been described in FIG. 6(a) for the sake of convenience. However, as illustrated in FIG. 6(c), in actuality, the label 306 is affixed to the blood collection tube 209. Because of this, the scattering of the infrared light on the surface of the label 306 and the absorption of the infrared light into the label 306 cause the amount of transmitted infrared light to be slightly attenuated in the portion where the label 306 exists (FIG. 6(d)). In contemplation of this, for the portion where the existence of the label 306 is detected by the light emitter/receptors 204a, 204a, the threshold value 605 in the region in which the label 306 exists is partially changed (lowered). As a result, even if the label 306 exists, a highly accurate detection of the liquid-level position is enabled. Then, by detecting the liquid-level position with high accuracy, as described above with reference to FIG. 5, the color information on the serum 303 can be correctly acquired to determine the category of the serum 303 with accuracy.

Figure 7:
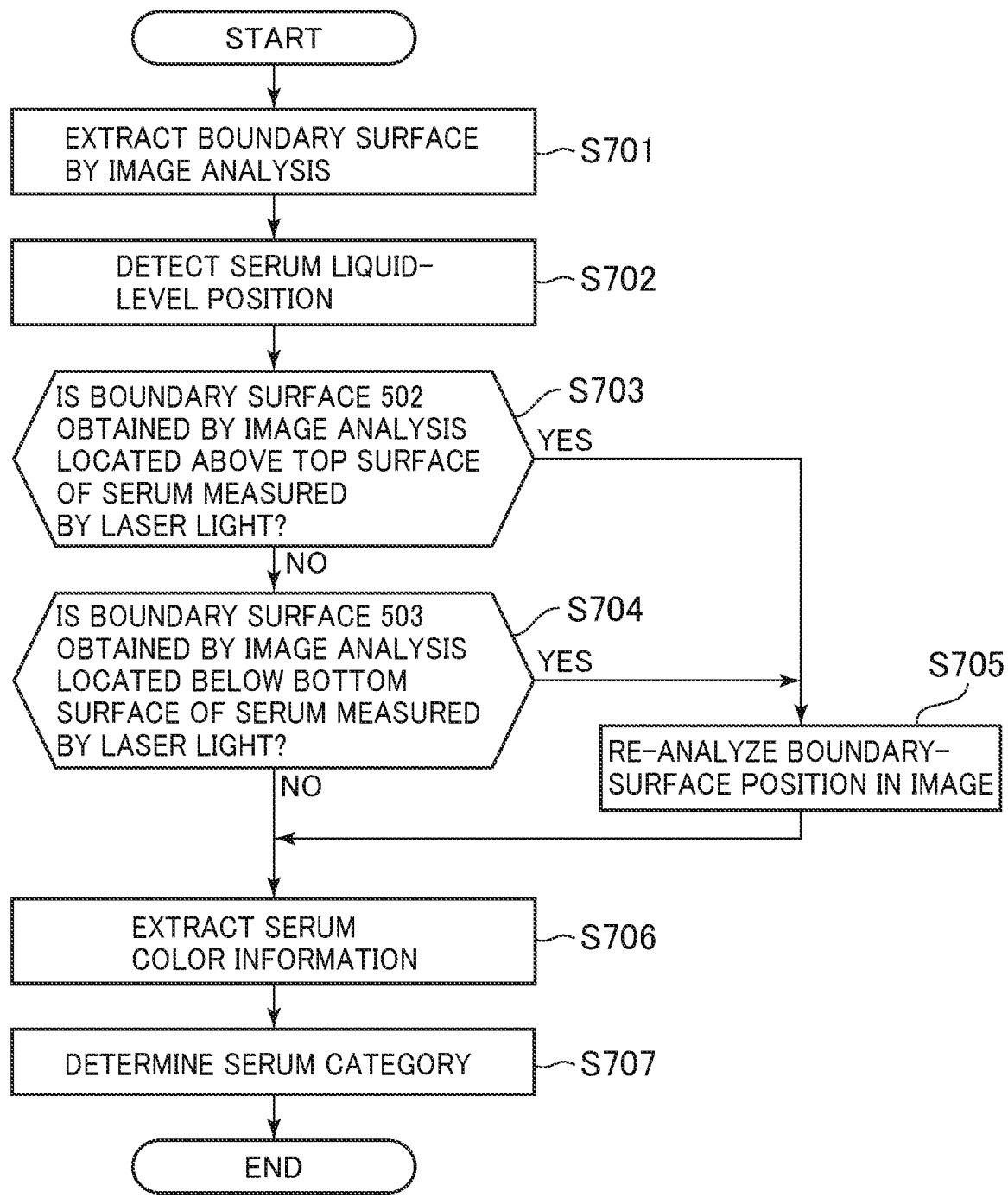
FIG. 7 is a flow of determining the category and the amount of serum in the biological sample analyzer in accordance with the first embodiment.

FIG. 7 illustrates a flow to determine a category and the amount of serum, performed in the biological sample analyzer 100 in accordance with the first embodiment. First, the image analysis is performed along the above-described flow in FIG. 4 in order to extract the boundary surfaces, 502 and 503 within the blood collection tube 209 (step S701). The positions of the boundary surfaces, 502 and 503 extracted at this stage are accumulated in the data accumulation section 205 as described above. It is noted that the label 306 is affixed to the surface of the blood collection tube 209. For information, the serum 303 which is the biological sample may be normal, but may possibly be hemolytic, jaundiced or chyous. Then, in such a case, it is likely that the correct boundary surfaces 502, 503 are not extracted as described above.

Concerning the blood collection tube 209 having been subjected to step S701, subsequently, the liquid-level position of the serum 303 is detected as described above with reference to FIG. 6 (step S702). The liquid-level position detected at this stage is accumulated in the data accumulation section 205 as described above. Then, the comparative analysis section 206 (see FIG. 2) performs a comparison between the liquid-level position and the boundary surfaces, 502 and 503 accumulated in the data accumulation section 205. Specifically, the comparative analysis section 206 determines first whether or not the boundary surface 502 obtained through the image analysis (see FIG. 5) is located above the top of the serum liquid level obtained by use of laser light (step S703).

When the condition is met (toward "Yes"), as described above with reference to FIG. 5(e), as in the region 507, the upper end extends beyond the actual region of the serum 303. And, if the color information on the serum 303 is extracted in this state, it is likely that color information on a portion except the serum 303 is incorrectly extracted. To address this, in this event, with consideration given to the serum liquid level obtained by use of the laser light (the liquid level detected by the liquid-level position detection section 203b), a re-analysis is performed on the boundary surfaces, 502 and 503 on the image acquired in step S701 as described above (step S705).

On the other hand, if it is determined in step S703 described above that the boundary surface 502 obtained through the image analysis (see FIG. 5) is absent above the top of the liquid level of the serum 303 obtained by use of the laser light (toward "No"), this implies that at least the top end of the region 504 is included in the region of the serum 303 as described above with reference to FIG. 5(b). Therefore, as the next step, the comparative analysis section 206 determines whether or not the boundary surface 503 obtained through the image analysis (see FIG. 5) is located below the bottom of the liquid level of the serum 303 obtained by use of the laser light (step S705).

If the condition is met (toward "Yes"), this implies that, as in the case of the contents described above with reference to FIG. 5(e), as in the region 507, the lower end extends beyond the actual region of the serum 303. And, if the color information on the serum 303 is extracted in this state, it is likely that color information on a portion except the serum 303 is incorrectly extracted. To address this, in this event, with consideration given to the liquid level of the serum 303 obtained by use of the laser light, a re-analysis is performed on the boundary surfaces 502, 503 on the image acquired in step S701 as described above (step S705).

On the other hand, if it is determined in step S704 described above that the boundary surface 503 obtained through the image analysis (see FIG. 5) is absent below the bottom of the liquid level of the serum 303 obtained by use of the laser light (toward "No"), this implies that at least the bottom end of the region 504 is included in the region of the serum 303 as in the case of contents described above with reference to FIG. 5(*b*). In short, if the above-described conditions in both step S703 and step S704 are not met, this implies that the region 504 obtained through the image analysis is included in the actual region of the serum 303. Therefore, the color information on the serum 303 can be extracted by extracting color information from any point within the region 504 in question. In other words, the determinations made above result in an identification of a determination target portion for a category of the serum 303 (region 504).

Thus, the comparative analysis section 206 extracts the color information of the serum 303 on the basis of at least one pixel value of those in the region 504 (i.e., a determination target portion for a category of the serum 303) between the boundary surface 502 and the boundary surface 503 which have been extracted in step S701 as described above (step S706). Here, by way of example, the color information acquired may be color information based on HSV which is similarly to how human perceive color. Of HSV system, for example, "H" representing hue indicates numerically a difference in attribute between colors such as red, yellow, green, blue and the like, and is shown numerically, for example, in a range from zero to 360.

And, the comparative analysis section 206 determines, based on the HSV-based color information thus extracted, which category the serum 303 belongs to (step S707). Specifically, the category determination for the serum 303 is performed by comparing the extracted hue value (the value of H in the HSV system) to a threshold value as a criterion. And, the threshold value is set for each of, for example, the normal, hemolytic, jaundiced and cylous serums 303, and it is determined based on the comparison what category the serum 303 belongs to.

It is noted that the determination performed here is not limited to the comparison to the preset threshold value. For example, a differentiation between biological-sample categories may be preset, and a pixel value of all the pixels in the detection target region or a representative value (a mean value of the pixel values of all the pixels or a median value of the pixel values in the detection target region, or the like) may be substituted into the discriminant, and then the resulting value may be used to determine a biological-sample category. With such a method, a serum color is able to be extracted with accuracy even if printing existing on the biological sample tube has a color similar to a color of the state of serum to be classified, such as, e.g., having a red color similar to hemolysis color, a brown or green color similar to jaundice color, and a white color similar to chyle color.

For information, if "Yes" is determined in step S703 and step S704, a warning or the like may be given to notify the laboratory technician or the like of the determination result. Also, if "Yes" is determined in step S703 and step S704, in step S701 and in step S702 a wrong determination is likely to be made in the stage of performing a determination of a label gap after a plurality of images is acquired. To avoid this, candidate images for determination of a label gap is displayed on a user I/F 208 (see FIG. 2, corresponding to the control personal computer 111 in FIG. 1) to cause the laboratory technician or the like to make a visual determination, and then a re-analysis and/or the like may be performed. As such, a higher reliability can be achieved.

As described above, the biological sample analyzer 100 performs liquid-level detection using a laser as described with reference to FIG. 6, in addition to the image analysis described above with reference to FIG. 3 to FIG. 5. In this manner, even if, in particular, a biological sample is apt to adhere to or remain near the inner wall of the blood collection tube 209, the liquid-level position can be detected with high accuracy.

Here, the inventors have collected and then centrifuged blood into the blood collection tubes 209 with the separating agent sealed to create pseudo specimens, and then carried out the flow in FIG. 7 using the resulting pseudo specimens. It is noted that a single prepared label 306 (with a barcode printed thereon) was affixed to each of the blood collection tubes 209 containing the pseudo specimens. As a result, in approximately 10% of the pseudo specimens thus created, a disparity has occurred between boundary surfaces, 502 and 503 obtained through the image analysis and a liquid-level position detected by use of the laser light, and therefore the process in step S705 has been performed. As a result, the percentage of the pseudo specimens of which a correct serum liquid level is extracted has been eventually increased to 95%, and for the remaining 5%, a warning could be notified to the laboratory technician or the like as described above. Thus, it has been shown that almost all of the pseudo specimens used in this process can be classified as some state or a warning can be notified to the laboratory technician or the like, and accordingly an improvement in classification accuracy is achieved.

Also, the biological samples may vary in tendency depending on regionality and nationality. For each anticipated location for use, a sample of which the sample category and the liquid volume are known may be prepared, and accordingly various techniques of such as changing detector parameters one by one, and the like. As such, higher reliability of detection is achieved.

In the first embodiment described above, on the assumption that all of the blood clots 304, the separating agent 302 and the serum 303 are contained in the blood collection tube 209, the category (normal, hemolysis, jaundice or chyle) of the serum 303 within the blood collection tube 209 is determined. However, in a second embodiment described below, the category of the serum 303 is determined with consideration given to the case of the blood collection tube 209 containing none of the blood clots 304, the separating agent 302 and the serum 303, that is, the blood collection tube 209 does not contain at least one of the blood clots 304, the separating agent 302 and the serum 303. The following is a description of a biological sample analyzer in accordance with the second embodiment.

It is noted that a biological sample analyzer used in the second embodiment is identical in configuration with the aforementioned biological sample analyzer 100 except for only control. Therefore, the biological sample analyzer used in the second embodiment is referred to, for the sake of convenience, as a "biological sample analyzer 200" which is omitted in the drawings. Also, the reference signs used below are the same as those used for the aforementioned biological sample analyzer 100.

FIG. 8 illustrates blood collection tubes 209 to be subjected to analysis in the biological sample analyzer 200 in accordance with the second embodiment, in which (a) represents a blood collection tube containing only the serum 303, (b) represents a blood collection tube containing the serum 303, the separating agent 302 and the blood clots 304, (c) represents a blood collection tube containing the serum 303 and the blood clots 304, (d) represents a blood collection tube containing the separating agent 302 and the blood clots 304, (e) represents a blood collection tube containing only the blood 305, (f) represents a blood collection tube containing the blood 305 and the separating agent 302, and (g) represents an empty blood collection tube (i.e., containing only air 301). In each of the blood collection tubes 209, an empty portion (an air-containing portion) is shown as "air 301". Incidentally, the label 306 is omitted in FIG. 8 for the sake of providing a clear description.

As described above, the blood collection tube 209 contains various components. Specifically, FIG. 8(a) illustrates the case of the serum 303 being divided by aliquoting, which is the case of containing only a liquid component. FIG. 8(b) illustrates the case of using the blood collection tube 209 with the separating agent 302 sealed therein to centrifuge the blood 305 (not shown in FIG. 8(b)). FIG. 8(c) illustrates the case of using the blood collection tube 209 without the separating agent 302 sealed therein (not shown in FIG. 8(c)) to centrifuge the blood 305 (not shown in FIG. 8(c)).

FIG. 8(d) illustrates the state after the serum 303 (not shown in FIG. 8(d)) is divided and removed by aliquoting, following the centrifugation of the blood 305 (not shown in FIG. 8(d)) by use of the blood collection tube 209 with the separating agent 302 sealed therein. FIG. 8(e) illustrates the state before the centrifugation of the blood 305 which has been collected in the blood collection tube 209 without the separating agent 302 sealed therein (not shown in FIG. 8(e)). FIG. 8(f) illustrates the state before the centrifugation of the blood 305 which has been collected in the blood collection tube 209 with the separating agent 302 sealed therein (not shown in FIG. 8(f)). FIG. 8(g) illustrates the state of the empty blood collection tube containing only the air 301.

As described above, types of the biological samples include the serum 303 and the blood clots 304 obtained through the centrifugation, and the like, as well as the blood 305 before the centrifugation. Further, some blood collection tubes 209 have the separating agent 302 sealed therein and also some blood collection tubes 209 have no separating agent 302 sealed therein. Moreover, some blood collection tubes 209 are not yet subjected to the centrifugation and some blood collection tubes 209 have been subjected to the centrifugation. To address such circumstances, the biological sample analyzer 200 in accordance with the second embodiment performs processing for classification of biological samples contained in the blood collection tubes 209, on the blood collection tubes 209 in such various conditions. Specifically, in the biological sample analyzer 200, a combination of the extraction of a boundary surface through the image analysis and the detection of a liquid-level position by the laser is used to determine a category (including an empty state) of the biological sample contained in the blood collection tube 209.

Figure 9:
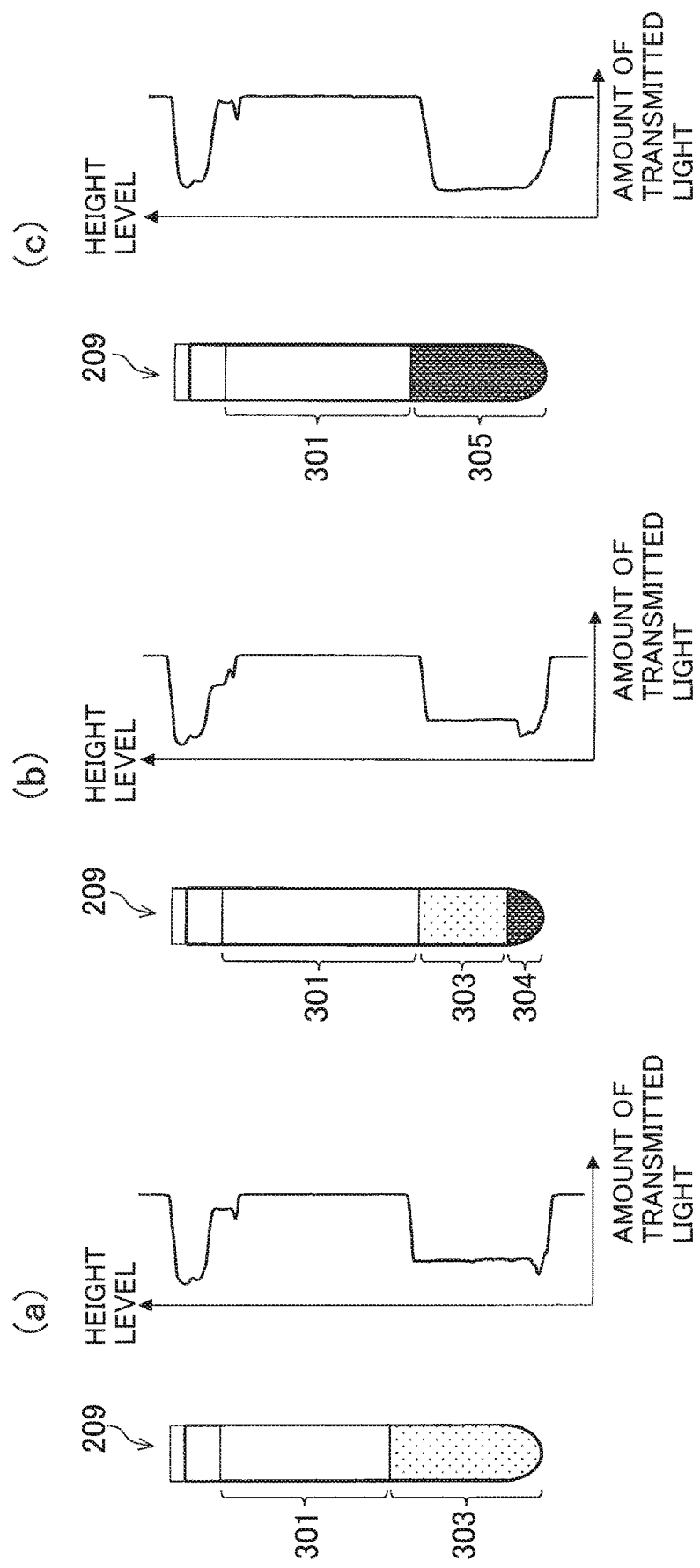
FIG. 9 illustrate diagrams explaining how to determine a liquid-level position by use of laser in the biological sample analyzer in accordance with the second embodiment, and also illustrates graphs each showing the relationship between the amount of transmitted light and the position in the length direction of the blood collection tube when the blood is collected into the blood collection tube containing no separating agent, in which (a) is pertinent to the blood collection tube illustrated in FIG. 8(*a*), (*b*) is pertinent to the blood collection tube illustrated in FIG. 8(*c*).

FIG. 9 illustrates diagrams explaining how to determine a liquid-level position by use of the laser in the biological sample analyzer 200 in accordance with the second embodiment, and also illustrates graphs each showing the relationship between the amount of transmitted light and the position in the length direction of the blood collection tube 209 (i.e., height level), in which (a) is pertinent to the blood collection tube 209 in FIG. 8(a), (b) is pertinent to the blood collection tube 209 in FIG. 8(c), and (c) is pertinent to the blood collection tube 209 in FIG. 8(e). It is noted that, in FIG. 9, for the sake of clear description, an evaluation performed on the blood collection tube 209 without the label 306. In actuality, however, an evaluation is performed on the blood collection tube 209 with the label 306 as in the case of the first embodiment described above. Then, the threshold values in the transmitted light profile (not shown in FIG. 9) are also varied depending on an affixation position of the label 306.

As described above with reference to FIG. 6, the serum 303 and the blood clots 304 absorb the infrared light. And, the blood 305 including water and blood cells also absorbs the infrared light. On the other hand, the air 301 and the separating agent 302 do not absorb the infrared light. Thus, where only the serum 303 and the blood clots 304 are contained (i.e., the separating agent 302 is not contained), and where the blood 305 and the separating agent 302 are contained, all of the serum 303, the blood clots 304 and the blood 305 absorb the infrared light, and in turn a large transmitted-light peak does not appear, so that it is difficult to obtain the transmitted light profile reflecting the liquid-level position. To address this, in the biological sample analyzer 200, the color information about the region other than the portion to which the label 306 is affixed (specifically, around the bottom of the blood collection tube 209) is extracted through the image analysis, thereby performing a determination of a type of the biological sample.

Figure 10:
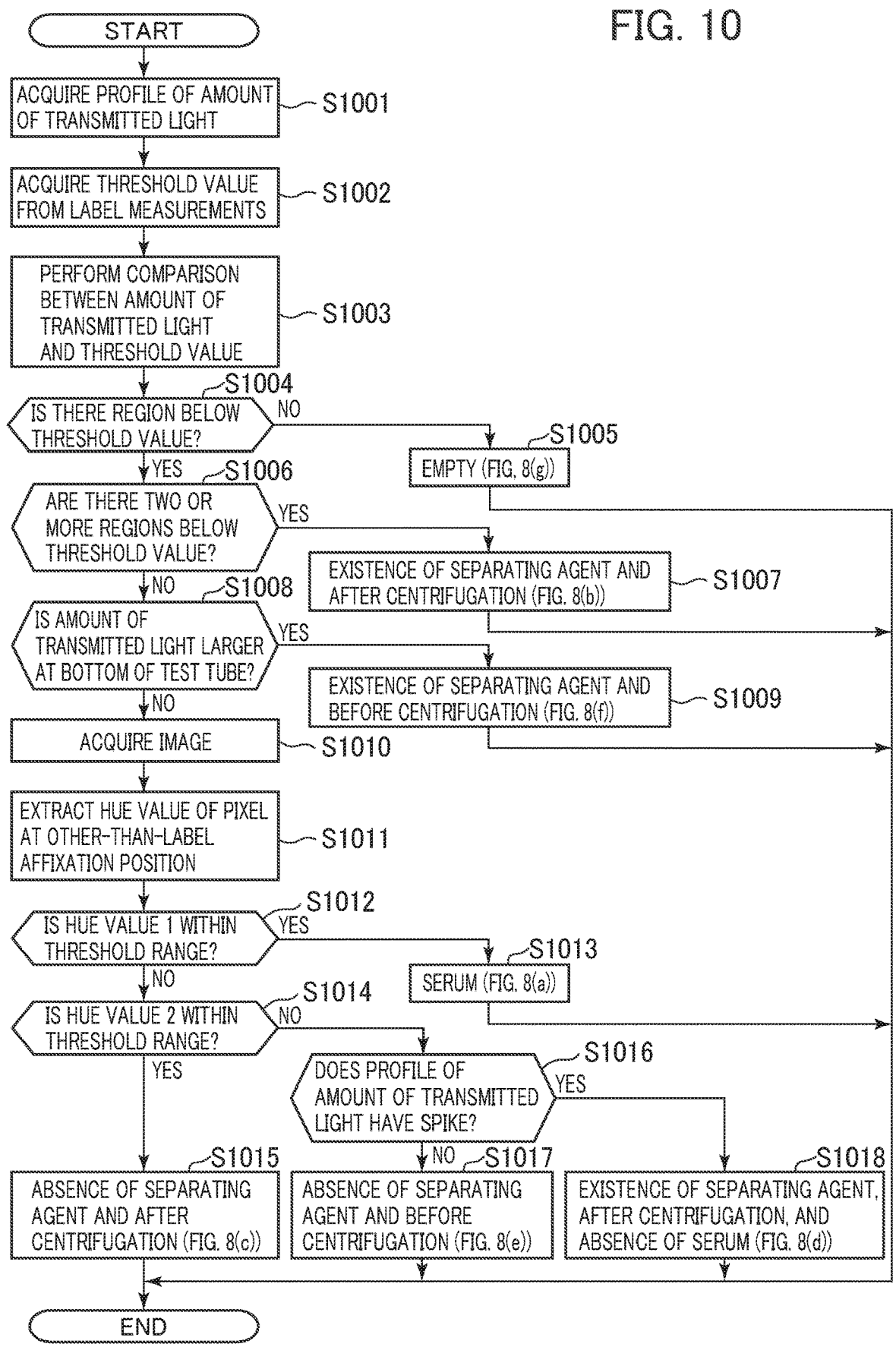
FIG. 10 is a flow of determining the category and the amount of a biological sample in the biological sample analyzer in accordance with the second embodiment.

FIG. 10 illustrates a flow of determining the category and the amount of a biological sample in the biological sample analyzer 200 in accordance with the second embodiment. The flow illustrated in FIG. 10 will now be described with additional reference to the figures referred to in the above-described first embodiment, as appropriate.

First, as in the case of the above-described biological sample analyzer 100, the liquid-level position detection section 203b (see FIG. 2) acquires a transmitted light profile of the biological sample in the blood collection tube 209 (see FIG. 6(d)) (step S1001). The transmitted light profile indicates a liquid-level position of the biological sample within a biological tube. Subsequently, as in the case of the above-described biological sample analyzer 100, the label position detection section 204b (see FIG. 2) detects the affixation position of the label 306 to perform the processing of lowering the threshold value by a certain value for the existence region of the label 306 (see FIG. 6(d)), and then acquires a threshold value entirely in the length direction (height direction) of the blood collection tube 209 (step S1002).

Subsequently, the comparative analysis section 206 (see FIG. 2) performs a comparison between the amount of transmitted light and the threshold value obtained in step S1002 (step S1003). Then, the comparative analysis section 206 determines whether or not there is at least one region in which the amount of transmitted light is below the threshold value (step S1004). If there is no region in which the amount of transmitted light is below the threshold value, it is determined that both the serum 303 and the blood clots 304 absorbing the infrared light do not exist. Because of this, the comparative analysis section 206 determines that a biological sample category is "empty" (see FIG. 8(g)), and the processing is terminated (step S1005).

On the other hand, if there is a region in which the amount of transmitted light is below the threshold value, at this stage, the comparative analysis section 206 determines how many such regions exist and whether or not the two or more regions exist (step S1006). Then, if there are two or more regions in which the amount of transmitted light is below the threshold value, this means that the separating agents 302 exist between the serum 303 and the blood clots 304. That is, a liquid level recognizable by a change in the amount of transmitted light exists between the blood clots 304 and the separating agent 302. And, a liquid level recognizable by a change in the amount of transmitted light also exists between the separating agent 302 and the serum 303. Because of this, the comparative analysis section 206 determines that a biological sample category is "existence of the separating agent 302, and after the centrifugation" (see FIG. 8(*b*)), and then the processing is terminated (step S1007).

Subsequently, the comparative analysis section 206 determines what amount of transmitted light is around the bottom of the blood collection tube 209 (step S1008). Specifically, it is determined whether or not the amount of transmitted light around the bottom of the blood collection tube 209 is larger than the threshold value. In this connection, because the blood collection tube 209 is formed of translucent or transparent materials, the major portion of infrared light passes through it. However, the blood collection tube 209 has a curved shape around its bottom, so that the incoming infrared light is strongly scattered to attenuate the amount of transmitted light. Because of this, whether or not to be around the bottom can be detected by detecting such attenuation. It is noted that, if the position of the bottom cannot be detected by this method, a point serving as a reference may be set at the time when the transmitted light profile is acquired.

If the amount of transmitted light around the bottom of the blood collection tube 209 exceeds the above-described threshold value (where the amount of transmitted light is larger), this means that the separating agent 302 exists around the bottom in the blood collection tube 209. Because of this, the comparative analysis section 206 determines that a biological sample category is "existence of the separating agent 302 and before the centrifugation" (see FIG. 8(*f*)), and the processing is terminated (step S1009).

On the other hand, if the amount of transmitted light around the bottom of the blood collection tube 209 is below the above-described threshold value (where the amount of transmitted light is smaller), the image processing section 201*b* (see FIG. 2) uses the camera 201*a* (see FIG. 2) to image the entire periphery of the blood collection tube 209, in order to acquire a plurality of images continuously (step S1010). The image acquisition at this step is performed by the same method as that described in the above-described first embodiment with reference to FIG. 3 and FIG. 4.

Subsequently, from the images thus acquired, the image processing section 201*b* extracts at least one piece of the color information (a hue (H) value in the aforementioned HSV system) of the blood collection tube 209 in the region other than the affixation position of the label 306 detected by the label position detection section 204*b* (see FIG. 2). Here, the image processing section 201*b* acquires a hue value of a pixel around the bottom of the blood collection tube 209 (the value will be hereinafter referred to as a "hue value 1"), and a hue value of a pixel in an area above the bottom of the blood collection tube 209 (the value will be hereinafter referred to as a "hue value 2"). As a result, in step S1011, the camera 201*a* is used to extract the existence region of the biological sample as an image. Then, based on this image and the transmitted light profile indicating the liquid-level position of the biological sample within the above-described blood collection tube 209 (see FIG. 9), a determination target portion (a portion at the bottom of the blood collection tube 209 and a portion above the bottom) for a category of the biological sample is identified.

It is noted that, as in the case of the above-described first embodiment, the extracted color information may also be used to calculate respectively the hue value 1 and the hue value 2 as a mean value of the pixel values, a median value of the pixel values or a pixel variance value. Also, the words "above the bottom" refers to anywhere as long as a point is between the inner bottom of the blood collection tube 209 and a lower end of the label 306 detectable by the label position detection section 204*b* (i.e., the label 306 does not exist below the lower end of question), and, for example, the point may be directly underneath the lower end of the label 306, and the like.

If the hue value 1 and the hue value 2 thus acquired are close to each other (e.g., if the ratio between the hue value 1 and the hue value 2 is within a predetermined given range), this means that the number of components of the biological sample in the region recognized by imaging is one. On the other hand, if the hue value 1 and the hue value 2 thus acquired are not close to each other (e.g., if the ratio between the hue value 1 and the hue value 2 is out of a predetermined given range), this means that there is an existence of a plurality of types of biological samples in the region recognized by imaging. Thus, the comparative analysis section 206 performs a comparison between the hue value 1 at around the bottom and the predetermined threshold range to determine whether or not the hue value 1 is in the threshold range (step S1012).

In this connection, a hue value indicates a difference in colors attribute. Therefore, a component of the biological sample in the region from which the color information is acquired can be estimated by comparison with the predetermined threshold range. For example, where the hue value 1 is expressed in a range from zero to 360, the threshold range for the hue value 1 may be defined from 30 to 120, and if the hue value 1 falls within the range from 30 to 120, it can be determined that the color of the biological sample near the bottom of the blood collection tube 209 is yellow or a color close to yellow.

If the determination result is that the hue value 1 falls within the above-described threshold range, this means that the color of the biological sample near the bottom of the blood collection tube 209 is yellow or a color close to yellow. Therefore, the comparative analysis section 206 determines that a biological sample category is "only serum" (FIG. 8(*a*)), and the processing is terminated (step S1013). However, if the hue value of the color information falls outside the above-described threshold range, the next processing in step S1014 will be performed.

In the step S1014, the comparative analysis section 206 performs a comparison between the hue value 2 at above near the bottom and a predetermined threshold range to determine whether or not the hue value 2 is within the threshold range. It is noted that, as in the above case of the hue value 1, again, for example, where the hue value 2 is expressed in a range from zero to 360, if the threshold range for the hue value 2 may be defined from 30 to 120, then this allows the determination of only the case where the color of the biological sample is yellow or a color close to yellow. Specifically, if the determination result is that although the biological sample exhibits a color other than a yellow color in around the bottom of the blood collection tube 209, in above the bottom the biological sample exhibits a color close to yellow, this result shows that a plurality of types of biological samples exists within the region recognizable by imaging. Then, in the determination result, if the hue value 2 is within the threshold range, the comparative analysis section 206 determines that the biological sample category is "absence of the separating agent and after the centrifugation" (FIG. 8(c)), and the processing is terminated (step S1015).

On the other hand, if the hue value 2 is outside the above-described threshold range, the following steps are performed. First, the comparative analysis section 206 returns to the transmitted light profile analysis using infrared light for determination. Where the sample is blood, a condition of the unclassified remainder is either the condition where the separating agent is absent and the centrifugation is yet to be performed (see FIG. 8(e)) or the condition where the separating agent exists, the centrifugation has been performed, and the serum is little contained by aliquoting (see FIG. 8(d)).

In the former (FIG. 8(e)), because the biological sample is uniform, the transmitted light profile exhibits approximately a constant value in the region in which the label 306 does not exist. On the other hand, in the later (FIG. 8(d)), because the biological sample contains the separating agent 302, the transmitted light profile undergoes a change in a portion corresponding to the separating agent 302 in the region in which the label 306 does not exist. Specifically, above the separating agent 302, the incoming light is scattered in the interface (liquid level) between the separating agent 302 and the air 301 or in the interface (liquid level) between the separating agent 302 and the serum 303. This causes attenuation of the transmitted light, and therefore a steep peak (so-called spike) occurs on the transmitted light profile.

In this regard, the comparative analysis section 206 determines whether or not the transmitted light profile exhibits a spike-like steep change in the amount of transmitted light (step S1016). If no spike is found (toward "No"), the comparative analysis section 206 determines that the biological sample category is "absence of the separating agent and before the centrifugation" (see FIG. 8(e)), and the processing is terminated (step S1017). On the other hand, if a spike is found (toward "Yes"), the comparative analysis section 206 determines that the biological sample category is "existence of the separating agent, after the centrifugation and absence of serum" (see FIG. 8(d)), and the processing is terminated (step S1018).

Using the above flow enables the determination of a category of a biological sample with high accuracy even if the label 306 exists on almost the entire periphery of the blood collection tube 209 and it is extremely difficult to be visually checked the inside of the blood collection tube 209.

Here, the inventors have carried out the flow in FIG. 10 using seven types of pseudo specimens which have been created to exhibit arrangements as illustrated above in FIG. 8, and classified the pseudo specimens into categories. It is noted that, in order to check if elimination of the influence of the label 306 is possible, as the blood collection tube 209 to be contain the pseudo specimen, three types of the blood collection tubes 209 in total have been used, namely, the blood collection tube 209 with the label 306 on the entire periphery for reference purposes, as well as the blood collection tube 209 with the label 306 on a part of the periphery and the blood collection tube 209 without the label 306. Consequently, the total number of pseudo specimens is 21.

By virtue of executing the processing of the flow illustrated in FIG. 10, 19 types of the 21 types of prepared specimens have been correctly determined, and the percentage of correct answers was about 90%. When compared with the determination using only the result of the liquid-level measurement (i.e., where the image analysis is not performed), this has increased the percentage of correct answers by about 30%. For the two types remaining of specimens for which the classification results have not been uniquely determined, the correct results have been achieved in the determination of presence and absence of the separating agent 302. Therefore, the determination as to whether or not the centrifugation has been performed can be performed on all the used pseudo specimens. As a result, for example, depending on a biological sample category that is determined based on the color information which is obtained from the result of the above-described image analysis, it can be determined whether or not the centrifugation module 103 illustrated above in FIG. 1 is used to perform the centrifugation.

Further, based on the biological sample category thus obtained, the next module to which the biological sample is to be moved is automatically determined, enabling efficient pre-processing. For example, the biological sample after the centrifugation is moved to the uncapping module 105, then the labeler module 106 and then the aliquot module 107 in this order, followed by being subjected to aliquoting. And, the sample classified into "existence of the separating agent and before the centrifugation" is moved to the centrifugation module 103 to be subjected to centrifugation. Furthermore, for the biological sample determined as empty, the user I/F 208 may be caused to display a warning.

It is noted that in the above-described embodiments, for example, blood, serum and the like illustrative of the biological sample are illustrated as a biological sample, but the biological sample may be, for example, urine and the like. Additionally, the present invention is capable of being practiced with any modification without departing from the scope and sprit of the present invention.

LIST OF REFERENCE SIGNS

100 . . . Biological sample analyzer
103 . . . Centrifugation module (centrifuge)
104 . . . Category determination module
200 . . . Biological sample analyzer
201a . . . Camera (imaging device, image analysis device)
201b . . . Image processing section (image analysis device)
203a1 . . . Light source (liquid-level detector)
203a2 . . . Photo receptor (liquid-level detector)
203b . . . Liquid-level position detection section (liquid-level detector)
204a . . . Light emitter/receptor (label position detector)
204b . . . Label position detection section (label position detector)
206 . . . Comparative analysis section (image analysis device,
liquid-level detector, comparative analysis device)
209 . . . Blood collection tube (biological sample tube)
302 . . . Separating agent
303 . . . Serum (biological sample)
304 . . . Blood clots (biological sample)
305 . . . Blood (biological sample)
306 . . . Label
605 . . . Threshold value

The invention claimed is:
1. A biological sample analyzer, comprising:
an imaging device that images a biological sample tube containing contents that includes a biological sample to obtain an image;
a liquid-level position detector that emits light toward the biological sample tube and detects emitted light having passed through the biological sample tube; and one or more processors that are coupled to the imaging device and the liquid-level position detector that are programmed to:

determine a category of the biological sample contained in the biological sample tube based on the following process and in the following order:

determine whether there are two or more regions of the contents in the biological sample tube above a predetermined threshold value based on a comparison between the light detected by the liquid-level position detector and the predetermined threshold value, determine whether an amount of the light detected by the liquid-level position detector in a bottom of the biological sample tube is greater than the predetermined threshold level, determine whether a first hue value of a first pixel at the bottom of the biological sample tube obtained from the image is within a first predetermined range, and determine whether a second hue value of a second pixel, which is an area of the image above the first pixel, is within a second predetermined range, wherein upon determining there are two or more regions of the contents in the biological sample tube that are above the predetermined threshold level, the category of the biological sample is after centrifugation with a separating agent, wherein upon determining the amount of the light detected by the liquid-level position detector in the bottom of the biological sample tube is greater than the predetermined threshold level, the category of the biological sample is before centrifugation with a separating agent, wherein upon determining the first hue value of the first pixel at the bottom of the biological sample tube obtained from the image is within the first predetermined range, the category of the biological sample is serum, wherein upon determining the second hue value of the second pixel is within the second predetermined range, the category of the biological sample is after centrifugation and without a separating agent, and wherein upon determining the second hue value of the second pixel is not within the second predetermined range, the category of the biological sample is before centrifugation and without a separating agent or after centrifugation with a separating agent and without serum.

2. The biological sample analyzer according to claim 1, wherein the one or more processors are programmed to: determine an existence region of the biological sample based on the image and a liquid-level position of the biological sample detected by the liquid-level position detector in order to identify a portion as a determination target for a category of the biological sample.

3. The biological sample analyzer according to claim 1, wherein the biological sample includes at least blood cell components, and wherein the liquid-level position detector emits light with a wavelength ranging from 0.7 μm or greater to 2.5 μm or less toward the biological sample tube, and wherein the one or more processors are programmed to: perform a comparison between the amount of transmitted light from the biological sample tube and the predetermined threshold value to detect a liquid-level position of the biological sample.

4. The biological sample analyzer according to claim 3, further comprising a label position detector that detects an affixation position of a label affixed to the biological sample tube, wherein the one or more processors are programmed to: change the predetermined threshold value according to the affixation position of the label detected by the label position detector.

5. The biological sample analyzer according to claim 1, further comprising a biological sample tube moving device that moves the biological sample tube in up-down directions, wherein the liquid-level position detector is secured to the biological sample analyzer, and wherein the one or more processors are programmed to: control the biological sample tube moving device to move the biological sample tube in at least one of the up-down directions, in order to allow the liquid-level position detector thus secured to detect a change in the amount of transmitted light from the biological sample tube, and based on the change, the liquid-level position detector detects a liquid level position of the biological sample.

6. The biological sample analyzer according to claim 1, further comprising a label position detector that detects an affixation position of a label affixed to the biological sample tube, wherein the label position detector emits visible light toward the biological sample tube from outside the biological sample tube, and measures the amount of light reflected in the biological sample tube, and wherein the one or more processors are programmed to: determine an existence or absence of affixation of the label and to detect an affixation position of the label based on the amount of light reflected in the biological sample tube.

7. The biological sample analyzer according to claim 1, further comprising:

a label position detector that detects an affixation position of a label affixed to the biological sample tube, and a biological sample tube moving device that moves the biological sample tube in up-down directions, wherein the label position detector is secured to the biological sample analyzer, and wherein the one or more processors are programmed to: control the biological sample tube moving device to move the biological sample tube in at least one of the up-down directions, in order to allow the label position detector thus secured to detect a change in the amount of light reflected in the biological sample tube, and detects an affixation position of the label.

8. The biological sample analyzer according to claim 1, wherein the one or more processors are programmed to calculate a liquid volume of the biological sample on the basis of the liquid-level position of the biological sample which has been detected.

9. The biological sample analyzer according to claim 1, further comprising a biological sample tube rotating device that rotates the biological sample tube in a circumferential direction, wherein the liquid-level position detector is secured to the biological sample analyzer, and wherein the imaging device secured continuously images the biological sample tube rotated by the biological sample tube rotating device.

10. The biological sample analyzer according to claim 1, wherein the biological sample tube contains therein at least serum as the biological sample, and wherein the one or more processors are programmed to acquire color information on the serum, and based on the color information acquired, determines to which of normal, hemolysis, jaundice and chyle the serum applies.

11. The biological sample analyzer according to claim 1, further comprising a centrifuge that centrifuges the biological sample contained in the biological sample tube, wherein, depending on a category of the biological sample determined based on the color information acquired by the comparative analysis device, centrifugation is performed on the biological sample by the centrifuge.

* * * * *